(12) United States Patent
Kadar et al.

(10) Patent No.: US 7,247,471 B2
(45) Date of Patent: Jul. 24, 2007

(54) SPIRAL PLEATED ROLLER BOTTLE

(75) Inventors: Anne M. Kadar, Wakefield, MA (US); Kenneth W. Whitley, Raleigh, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 59 days.

(21) Appl. No.: 10/742,308

(22) Filed: Dec. 19, 2003

(65) Prior Publication Data
US 2004/0241836 A1 Dec. 2, 2004

Related U.S. Application Data

(60) Provisional application No. 60/505,742, filed on Sep. 25, 2003, provisional application No. 60/437,748, filed on Jan. 2, 2003.

(51) Int. Cl.
*C12M 1/34* (2006.01)

(52) U.S. Cl. .............................. 435/288.1; 435/304.1; 215/382; 215/900

(58) Field of Classification Search ................ 215/382, 215/379; 220/666; 435/288.1, 304.1
See application file for complete search history.

(56) References Cited

U.S. PATENT DOCUMENTS 4,962,033 A * 10/1990 Serkes et al. ................ 435/395
5,370,250 A * 12/1994 Gilbert ............................ 222/1

\* cited by examiner

*Primary Examiner*—David Redding

(57) ABSTRACT

A roller bottle is provided with a bottom wall, a top wall and a cylindrical side wall extending between the bottom and top walls. The top wall includes an opening to provide access to the interior of the roller bottle. The cylindrical side wall of the roller bottle is formed with at least one spiral pleat extending substantially from the bottom to the top for increasing cell growth surface area and for facilitating the flow of liquid to all interior surface areas of the bottle as the bottle is rolled about its longitudinal axis.

13 Claims, 3 Drawing Sheets

SPIRAL PLEATED ROLLER BOTTLE

RELATED APPLICATIONS

This application claims priority from U.S. Provisional Patent Application Ser. No. 60/505,742 filed on Sep. 25, 2003, and from U.S. Provisional Patent Application Ser. No. 60/437,748, filed on Jan. 2, 2003.

BACKGROUND OF THE INVENTION

1. Field of the Invention

This invention relates to a container for cell culture production, and, more particularly, to a roller bottle having at least one angled exterior pleat for achieving a high cell growth surface area on the interior of the bottle and for facilitating access to all surface areas by liquids deposited in the bottle.

2. Description of the Related Art

One type of container commonly used in laboratories for culturing cells is know as a "roller bottle". Roller bottles are generally cylindrical and are adapted to rotate about their vertical axes. The internal surfaces of such roller bottles provide active regions for culturing cells. A liquid growth medium is introduced into the roller bottle. The rotating movement of the bottle keeps the internal surfaces wetted with the liquid medium, thereby encouraging the growth of cells.

Rotating rollers of an appropriate apparatus rotate these roller bottles. It is desirable to grow large amounts of cells, mostly for cell by-products, such as pharmaceutical substances that are secreted by cells. Various approaches have been used to increase the internal surface area of roller bottles. One approach has been to increase the amount of actual surface area available for cell growth.

Some roller bottles are produced unitarily by a blow-molding technique and include longitudinal pleats in the walls of the roller bottle. The longitudinal pleats increase the effective internal surface area of the roller bottle, and extend into the growth chamber for increasing culture or cell yield.

It is further known to provide a culture vessel having such longitudinal pleats, and further including circumferential collars that encircle the external surface of the top and bottom ends of the vessel. The collars maximize the vessel's grip point when the vessel is placed on its side on the rollers of a rotating apparatus such as a roller rack.

The prior art also discloses a roller bottle having pleats perpendicular to the longitudinal axis of the bottle for increasing the surface area for growing cells and further including at least one unpleated longitudinal drain panel. Reinforcing ribs on the exterior of the bottle parallel to the longitudinal axis of the bottle extend along the outer edge of the cross-wise corrugation for strengthening the pleated bottle.

It is also known to use circumferential ribs on a roller bottle for reinforcing the bottle walls. In this regard, the prior art discloses a roller bottle having flexible plastic walls and a plurality of spaced-apart circumferential reinforcement rings defined in the flexible plastic walls to cause the body to retain a generally cylindrical shape.

A problem associated with prior art roller bottles, especially those having pleats for expanding the surface area for growing cells, has been the tendency of the bottle walls to expand when the insides of the bottles become pressurized. This expansion causes the bottle to stop rolling on a roller rack. The absence of rotation causes portions of the surfaces to become dry and promotes cell death in these dry areas.

Another problem associated with prior art roller bottles relates to the ability to assure that liquid placed in the roller bottle will achieve maximum contact with all interior surface regions of the pleated walls. In this regard, it has been determined that roller bottles with circumferential pleats will distribute liquid efficiently within any given pleat as the roller bottle is rotated about its axis. However, liquid may not be distributed uniformly among the various circumferential pleats. Although longitudinal pleats allow liquid to flow longitudinally along the grooves defined by the pleats, rotation of such a longitudinal-pleated roller bottle about its longitudinal axis does not always distribute liquid efficiently from one longitudinal pleat to another, and also results in increased agitation of the liquid, which is detrimental to cell growth and cultivation.

It is desirable therefore to provide a pleated roller bottle which safeguards against bottle expansion under pressure to thereby allow the roller bottle to continue rolling on a roller rack.

It is also desirable to provide roller bottles with a pleat arrangement that permits efficient flow of liquid to all surface areas defined by the pleats while maintaining agitation of the liquid.

SUMMARY OF THE INVENTION

The present invention provides a roller bottle for cell growth culturing including an elongate cylindrical side wall, a closed bottom end and an opening at an opposing top end. The elongate cylindrical wall includes at least one helical or spiral pleat that extends from proximate the top end to proximate the bottom end. The elongate cylindrical side wall may further include a longitudinal smooth surface or two diametrically opposed longitudinal smooth surfaces that run the length of the bottle.

The spiral or helical pleat provides an advantage over circumferential pleats when cells are harvested from the bottle. In particular, cells are collected from the bottle by first pouring off the liquid growth medium and then detaching the cells from the bottle walls. Frequently, a trypsin solution is poured into the bottle and then distributed around the inside of the bottle to cover all of the cells. A continuous helical or spiral pleat path running substantially the entire length of the bottle enables the trypsin to more easily reach all of the cells because the trypsin can follow a continuous path around the pleat as the bottle is rotated about its axis. In contrast, circumferential pleats or longitudinal pleats may complicate uniform distribution of trypsin to all areas of the bottle from which cells may be harvested. Thus, a much more thorough coating with trypsin is achieved with a spiral or helical pleat.

Other objects and features of the present invention will become apparent from the following detailed description considered in conjunction with the accompanying drawings. It is to be understood, however, that the drawings are designed solely for purposes of illustration and not as a definition of the limits of the invention. It should be further understood that the drawings are not necessarily drawn to scale and that, unless otherwise indicated, they are merely intended to conceptually illustrate the structures and procedures described herein.

BRIEF DESCRIPTION OF THE DRAWINGS

In the drawings wherein like reference characters denote similar elements throughout the several views.

DETAILED DESCRIPTION OF THE INVENTION

Figure 1:
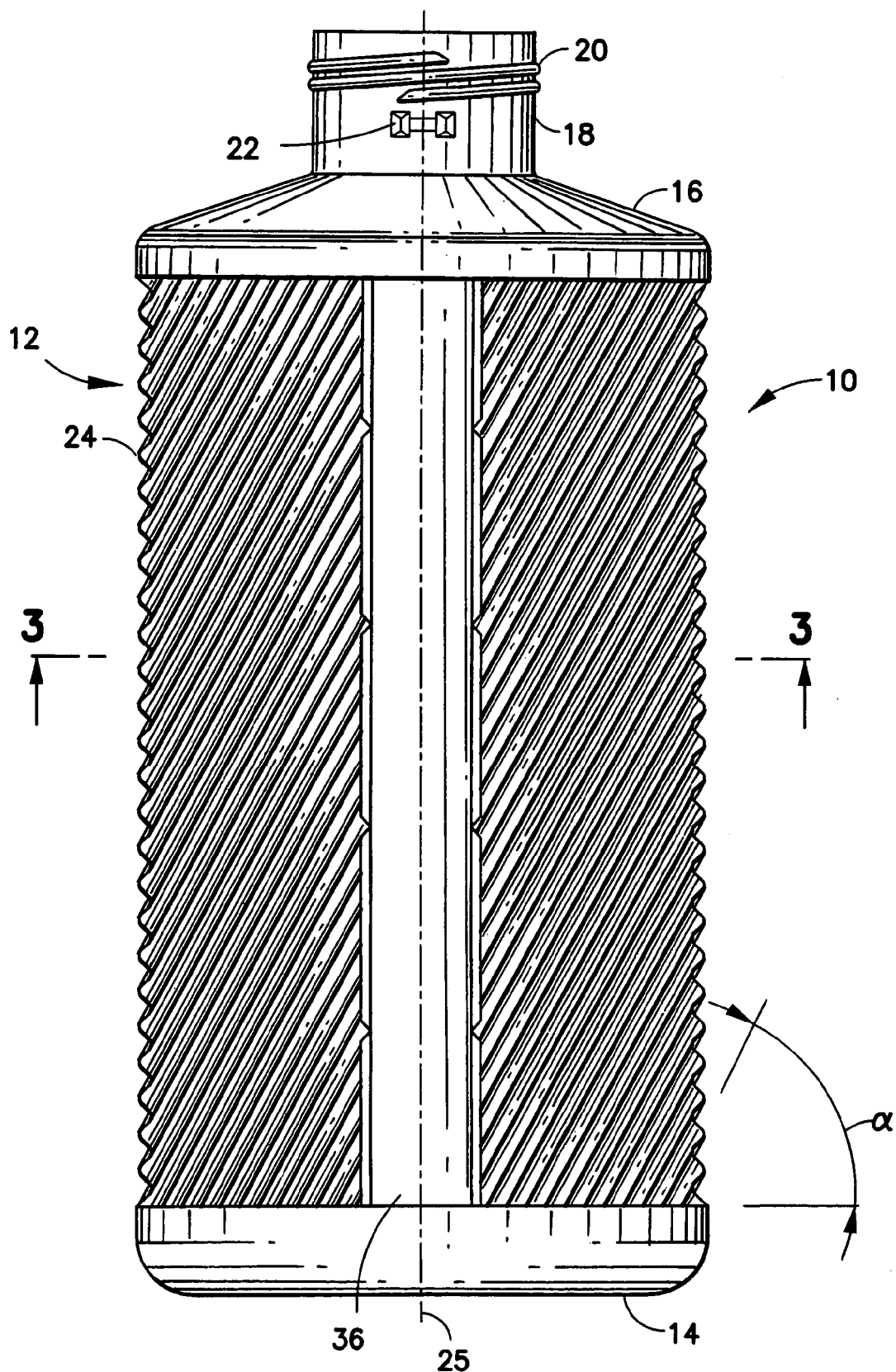
FIG. 1 is a side elevational view of a roller bottle in accordance with the present invention.

A roller bottle 10 in accordance with the present invention is shown in FIGS. 1-4. Roller bottle 10 includes a generally cylindrical side wall 12 which extends between proximate a top wall 16 and proximate a bottom wall 14. Extending from top wall 16 and integral therewith is a neck 18 having extended screw threads 20 for receiving an internally threaded screw cap (not shown) thereon in the usual manner. Other cap connections, such as bayonet connections, may be used. Neck 18 may include a locking arrangement 22 for holding a cap in a locked open position on the roller bottle for maintaining the roller bottle open to the environment.

As described above, a problem associated with prior art roller bottles that have longitudinal pleats is that the pleats tend to expand when the inside of the bottle becomes pressurized. This may occur when the roller bottle is sealed and warmed in an incubator, resulting in an elevation of the internal bottle pressure, typically by about 0.069 BAR (1 psi). The internal pressure in the roller bottle may cause the walls to bow outward which causes the bottle to stop rolling on the roller rack. As a result, portions of the interior surface of the bottle become dry while other portions of the interior surface of the bottle stay immersed, leading to cell death and a reduction in culture yield.

Roller bottle 10 addresses the problem of side wall expansion by providing at least one helical or spiral pleat 24 arranged on the surface of the bottle at an offset angle with respect to the longitudinal axis of the bottle 10. Pleats 24 are, thus, arranged in a substantially "spiral" or helical layout about the bottle side wall 12. Preferably, pleats 24 extend between a vertical location substantially below and proximate to top wall 16, and a vertical location substantially above and proximate to bottom wall 14, i.e., about 0.6 cm (0.25 inches) from the top and bottom, respectively.

In accordance with the invention, the pleat can take the form of a single helical spiral (pleat 24a in FIG. 2) which runs between the top and bottom of bottle 10. In this case, the single spiral has a very shallow angle "$\theta$" with respect to a plane cutting perpendicularly through the longitudinal axis 25 of bottle 10 (a "horizontal axis"), for example in the range of from about 2° to about 10°. As the angle of pleat 24 increases with respect to the horizontal axis, the width of pleat 24 should be increased, otherwise a "blank" spot between adjacent turns of the pleat will exist. Preferably, additional pleats 24 should be added to maximize the surface coverage of bottle 10 and provide sufficient cell cultivation area as shown in of FIG. 1.

As seen in FIG. 1, each pleat 24 is oriented at an angular pitch "$\alpha$" relative to the horizontal axis of the bottle 10, wherein angle "$\alpha$" ranges between 45° and 70° with respect to the horizontal axis, and is at about 65°.

Figure 3:
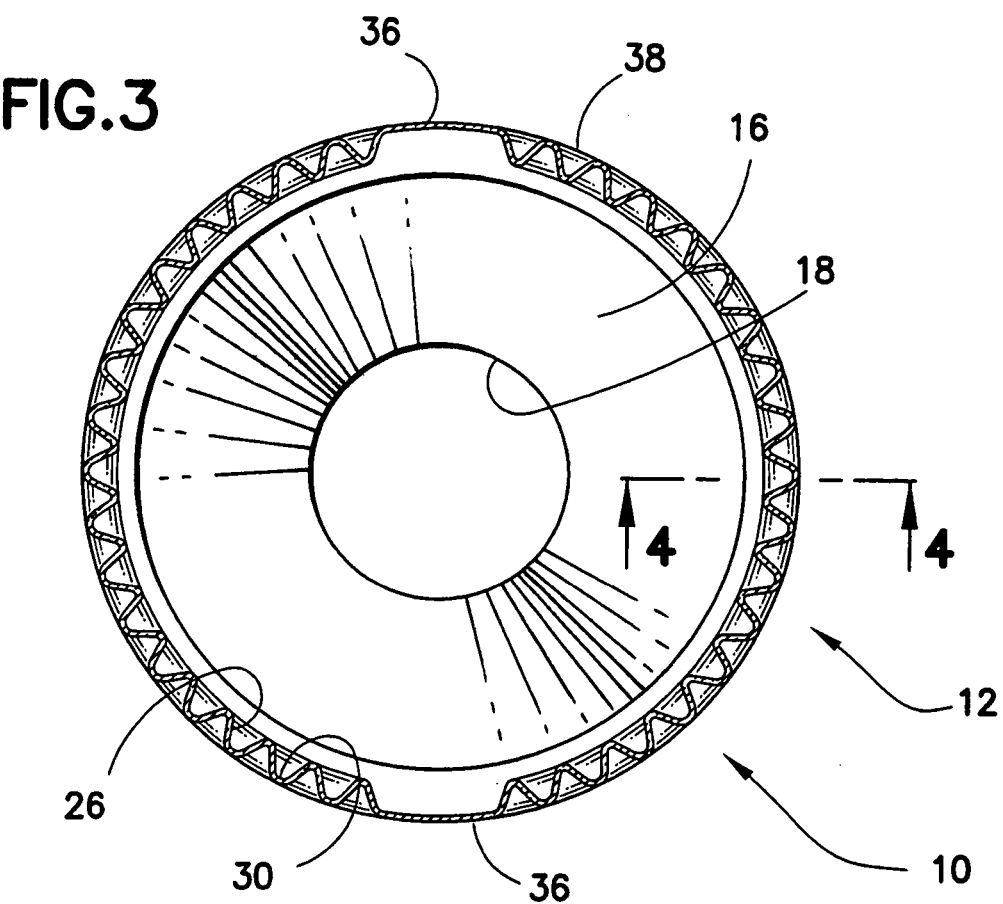
FIG. 3 is a horizontal sectional view of the roller bottle of FIG. 1 taken along line 3-3 of FIG. 1.
Figure 4:
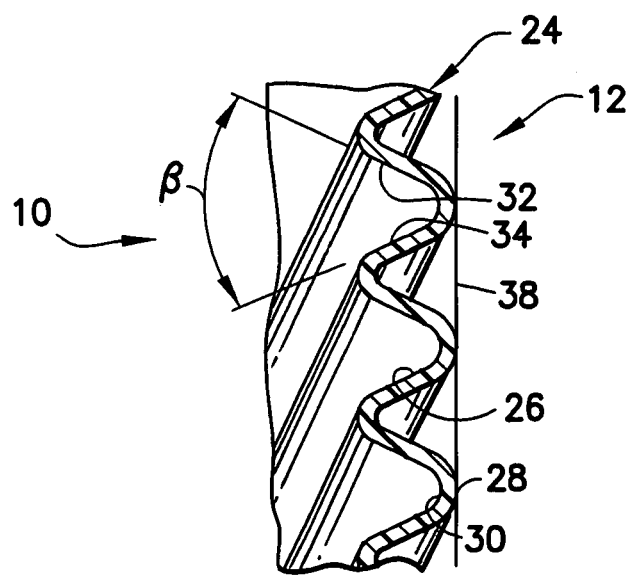
FIG. 4 is a cross-sectional view of the roller bottle of FIG. 1 taken along line 4-4 in FIG. 3.

Spiral pleats 24 provide a reinforcing effect similar to the circumferential pleats of the prior art. As can be seen in FIGS. 3 and 4, pleats 24 provide a plurality of opposed facing internal surfaces 26 for the formation of cell growth. Thus, the pleated structure increases the internal active surface area of roller bottle 10 while safeguarding against deformation of the bottle when pressurized to prevent cessation of bottle rotation on a roller rack.

While the present invention may be constructed in various sizes and configurations, the structure of the present roller bottle includes a bottle which is approximately 27.08 cm (10.66 inches) in length from the top of neck 18 to the bottom of base 14. Such a configured bottle defines a growth surface area length of about 22.86 cm (9.0 inches) having a diameter of about 11.76 cm (4.63 inches). As shown in FIG. 4, the internal surfaces 26 formed by the pleats 24 represent a generally wave-like structure having outer and inner apices 28 and 30, respectively. Outer apices 28 extend to a circumference 38 (see FIG. 3). Inner apices 30 form interior channels on the inner surface of bottle 10, thereby permitting laminar flow of the liquid growth medium therethrough. The period defined between adjacent outer apices 28 is approximately 0.05 cm (0.195 inches). Opposing or facing internal surfaces 26 (shown as surfaces 32 and 34) of adjacent spiral pleats 24 define an angle "$\beta$", which may be approximately 42°. Inner apices 30 of pleats 24 are desirably rounded to facilitate cell adherence to internal surfaces 26. Moreover, such rounded surfaces are easy to form by casing or molding and are stronger and less subject to cracking if flexed.

Figure 2:
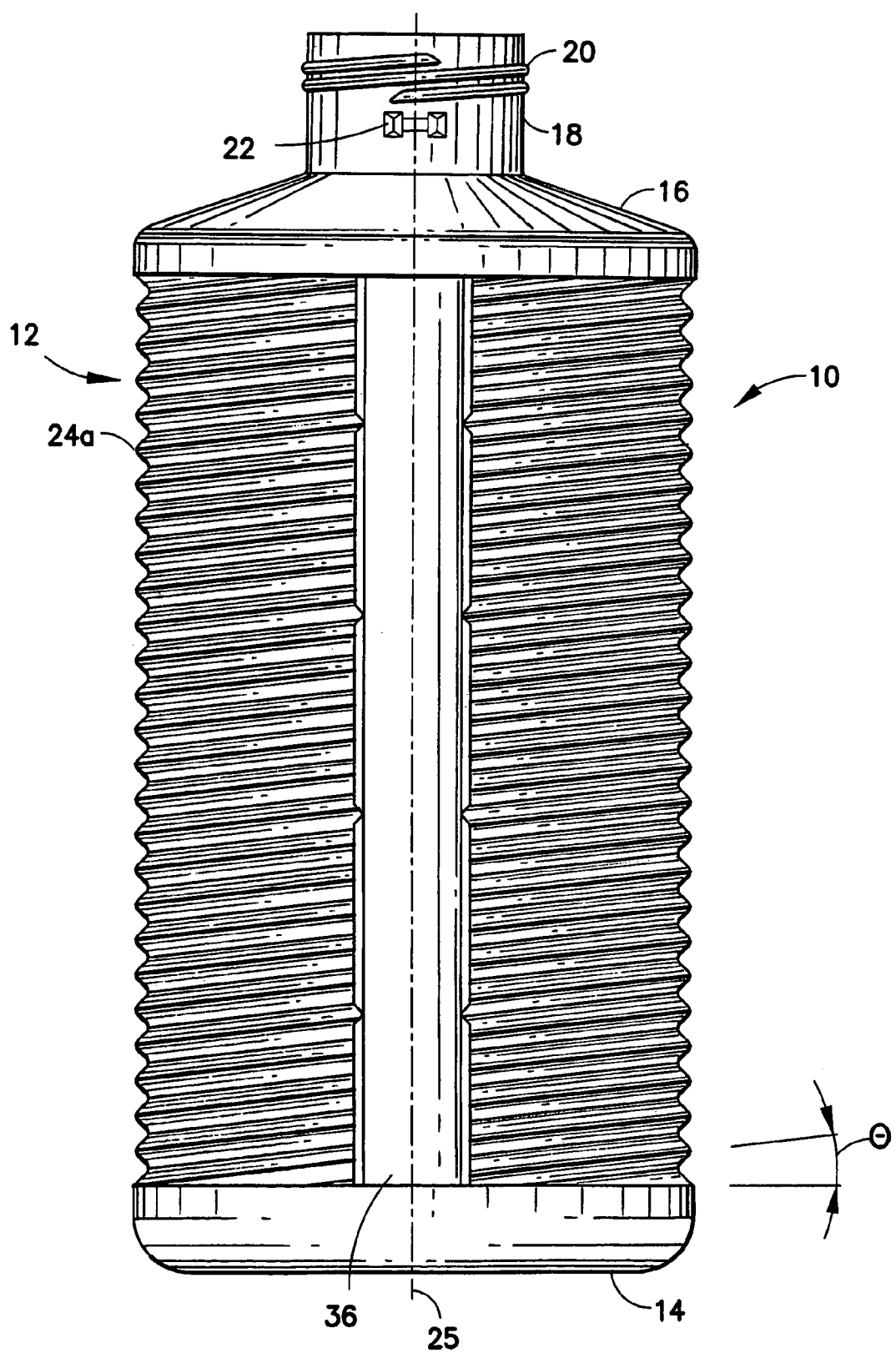
FIG. 2 is a side elevational view of a roller bottle in accordance with a secondary version of the present invention.

As shown in FIGS. 1-3, roller bottle 10 may further include diametrically opposed longitudinally extending smooth sections, or lands, 36 that interrupt pleats 24 to enhance the microscopic viewing of the contents of roller bottle 10 and/or to facilitate culturing of cells. In various embodiments of the present invention, the roller bottle contains two diametrically opposed smooth sections 36 to facilitate microscopic viewing. The particular arrangement of smooth sections 36 shown in the drawings is not critical. Moreover, the width of smooth sections 36 is not critical, except that these panels also decrease the amount of internal surfaces 26 which are used for cell growth. Each smooth section 36 may be between about 5.715 cm (2.25 inches) and about 7.62 cm (3 inches) in length, measured circumferentially. Pleats 24 are approximately 0.02 cm (0.079 inches) deep, when measured radially from circumference 38.

It is noted that roller bottle 10 may include a recessed portion (not shown) in bottom wall 14 to facilitate stacking of roller bottle 10 with a similar bottle in a nesting relationship.

The spirally pleated roller bottle 10 of the present invention can be used to increase the culture or cell yields per unit for either adherent-type cells or cells that grow in suspension. It is noted that adherent-type cells include cells which require a support surface to grow on, as well as cells capable of growing on a support surface. By the phrase "increase the culture or cell yields", it is meant that there is an increase in the number of cells and/or their by-products per culture vessel or unit. As shown in the drawings herein, cylindrical side wall 12 of roller bottle 10 has a plurality of spiral pleats 24 (shown in FIG. 1) or a plurality of turns of a single spiral pleat 24a as in FIG. 2, along a substantial portion of the length of the bottle, thus corrugating interior surfaces 26. The interior pleating increases the surface area available for the attachment and growth of adherent-type cells, thus increasing the culture or cell yields per vessel.

After cells have formed on internal surfaces 26 of roller bottle 10 by rolling the bottle in the proper environment for the formation of the cells, roller bottle 10 with formed cells on the walls thereof is removed from a roller rack. The cell forming liquid medium remaining in bottle 10 may be decanted from bottle 10 along pleats 24 and smooth sections 32. A small amount of saline solution may be added to wash the cells of lingering medium components. Alternatively, the liquid medium may remain in the bottle if it is only present in a small amount.

A more conventional procedure for removing cells is by introducing a solution containing the proteolytic enzyme trypsin, together with a chelating agent, which has the effect of causing the cells to release from internal surfaces 26 for decanting from roller bottle 10 along spiral pleats 24 and longitudinal smooth sections 32. More particularly, spiral pleats 24 ensure that the trypsin solution follows the spiral paths formed by pleats 24 from the top end 16 to the bottom end 14 of the bottle 10 merely by rotating bottle 10 about its longitudinal axis 36. Hence, complete exposure to the trypsin solution is assured, thereby maximizing cell yield. Subsequently, roller bottle 10 may be discarded.

Thus, the advantage of providing a roller bottle 10, such as that of the present invention, which may be inexpensively produced by blow-molding, used once, and then discarded, is readily apparent. The inventive roller bottle 10 provides a unitary structure including an elongate cylindrical wall with spiral pleats that provide a greatly increased surface area for cell growth formation. The spiral pleats on the cylindrical wall further reinforce the bottle walls and eliminate the need to discard the roller bottle prematurely during culturing due to repeated flexing of the pleats which can cause fatigue and cause the bottle to stop rolling on the roller rack, especially during long periods of use in connection with a cell culturing batch process. Spiral pleats 24 reinforce the structure of roller bottle 10 and prevent the bending and extension of side wall 12.

In viewing generally the conditions for producing roller bottles in accordance with the invention, a variety of thermoplastic materials may be utilized including, for example polystyrene, polyethylene terephthalate, the polyolefins and polyvinyl chloride. Polystyrene is particularly desirable as cells appear to grow well and in large numbers on this material.

The wall of the bottle should have a sufficient thickness to provide a bottle with adequate strength when filled with a liquid. Typically, the material used for forming the bottle should have a thickness of about 0.0236 inches (0.06 cm) for a 2.25 liter roller bottle. The thermoplastic resin used for forming bottles by extrusion, blow or injection blow-molding techniques should be able to readily flow to form the spiral pleats.

It is noted that various embodiments of the invention have been described and that numerous substitutions, modifications and alterations are permissible without departing from the spirit and scope of the invention. For example, a cross-hatched pattern of intersecting spiral pleats could be used. Moreover, a bottle having flat side wall sections approximating a cylinder, e.g., an octagon-shaped horizontal cross-section, can be employed instead of the cylindrical bottles depicted in the figures. The design must be such that the bottle is not hindered from rolling on its vertical axis when placed on a rolling apparatus.

It will be understood that various omissions and substitutions and changes in the form and details of the devices illustrated, and in their operation, may be made by those skilled in the art without departing from the spirit of the invention. For example, it is expressly intended that all combinations of those elements which perform substantially the same function in substantially the same way to achieve the same results are within the scope of the invention. Moreover, it should be recognized that structures and/or elements shown and/or described in connection with any disclosed form or embodiment of the invention may be incorporated in any other disclosed or described or suggested form or embodiment as a general matter of design choice.

What is claimed is:

1. A roller bottle for use in culturing cells, comprising:
   a bottom;
   a top; and,
   a continuous side wall extending between said bottom and said top, said side wall having an interior surface and an exterior surface, and being spaced about a longitudinal axis of said bottle for allowing said bottle to rotate along said side wall about the longitudinal axis for distributing, along said side wall, a liquid medium contained in said bottle to wet said side wall, said side wall including at least one pleat extending from a first point proximate said top to a first point proximate said bottom, said pleat being arranged at an angle offset with respect to a plane perpendicular to the longitudinal axis of said bottle, said pleat defining at least one interior channel on said inner surface of said side wall for permitting laminar flow and distribution of said liquid along said pleat, said interior channel providing a surface for culturing the cells, wherein at least one smooth land is formed in said side wall, said land interrupting said pleat.

2. The bottle of claim 1, wherein said angle is in the range of about 2° to about 70°.

3. The bottle of claim 2, wherein said pleat is a single helical pleat.

4. The bottle of claim 3, wherein said angle is in the range of about 2° to about 10°.

5. The bottle of claim 2, wherein said at least one pleat comprises a plurality of substantially parallel pleats.

6. The bottle of claim 5, wherein said angle is in the range of about 40° to about 70°.

7. The bottle of claim 6, wherein said angle is approximately 65°.

8. The bottle of claim 1, wherein said land runs between a second point proximate said top and a second point proximate said bottom.

9. The bottle of claim 8, wherein said land is substantially arcuate, and lies in a cylindrical plane of generally constant distance from the longitudinal axis of said bottle.

10. The bottle of claim 9, wherein said exterior surface of said pleat includes apices extending to a generally cylindrical plane co-incident with said plane of said land.

11. The bottle of claim 1, wherein said pleat is approximately 0.079 inches deep.

12. The bottle of claim 1, wherein said interior channel has a substantially uniform width.

13. The bottle of claim 12, wherein said interior channel is approximately 0.195 inches wide.

* * * * *